US010550226B2

(12) United States Patent
Valsecchi et al.

(10) Patent No.: US 10,550,226 B2
(45) Date of Patent: Feb. 4, 2020

(54) CYCLOPHOSPHAZENE DERIVATIVES

(71) Applicant: SOLVAY SPECIALTY POLYMERS ITALY S.P.A., Bollate (IT)

(72) Inventors: Roberto Valsecchi, Verdellino (IT); Fabrizio Mutta, Fino Mornasco (IT)

(73) Assignee: SOLVAY SPECIALTY POLYMERS ITALY S.P.A., Bollate (MI) (IT)

( * ) Notice: Subject to any disclaimer, the term of this patent is extended or adjusted under 35 U.S.C. 154(b) by 338 days.

(21) Appl. No.: 15/510,559

(22) PCT Filed: Sep. 8, 2015

(86) PCT No.: PCT/EP2015/070427
§ 371 (c)(1),
(2) Date: Mar. 10, 2017

(87) PCT Pub. No.: WO2016/037998
PCT Pub. Date: Mar. 17, 2016

(65) Prior Publication Data
US 2017/0260327 A1    Sep. 14, 2017

(30) Foreign Application Priority Data

Sep. 10, 2014  (EP) .................... 14184247

(51) Int. Cl.
*G11B 5/725* (2006.01)
*C08G 65/335* (2006.01)
*C07F 9/6593* (2006.01)
*C10M 107/38* (2006.01)

(52) U.S. Cl.
CPC ...... *C08G 65/3356* (2013.01); *C07F 9/65815* (2013.01); *C10M 107/38* (2013.01); *G11B 5/725* (2013.01); *C08G 2650/48* (2013.01); *C10M 2213/0606* (2013.01); *C10N 2240/204* (2013.01)

(58) Field of Classification Search
CPC ............ C08G 65/3356; C07F 9/65815; C07F 9/65814; C07F 9/65817; C07F 9/65812; C10M 107/38; C10M 2213/0606; G11B 5/725; C10N 2240/204
See application file for complete search history.

(56) References Cited

U.S. PATENT DOCUMENTS

| 2002/0183211 A1 | 12/2002 | Akada et al. |
| 2008/0020171 A1 | 1/2008 | Wakabayashi et al. |
| 2008/0305975 A1 | 12/2008 | Liu et al. |
| 2009/0318664 A1 | 12/2009 | Yang et al. |
| 2012/0219826 A1 | 8/2012 | Li et al. |
| 2012/0251843 A1 | 10/2012 | Yan et al. |
| 2012/0276417 A1 | 11/2012 | Shimokawa et al. |

FOREIGN PATENT DOCUMENTS

| WO | 2007043450 A1 | 4/2007 |
| WO | 2009043928 A1 | 4/2009 |

OTHER PUBLICATIONS

Kang H.H. et al., "The Use of Cyclic Phosphazene Additives to Enhance the Performance of the Head/Disk Interface", Lubrication Engineering (Journal of the Society of Tribologists and Lubrication Engineers), Mar. 1999, vol. 55(3), p. 22-27.

*Primary Examiner* — Holly C Rickman

(57) ABSTRACT

The present invention relates to a phosphazene compound [compound (L)] comprising a cyclophosphazene central core wherein each phosphorus atom of said core bears a substituent independently selected from: a) a chain (A), said chain (A) comprising a (per)fluoropolyether chain [chain $(R_f)$], one or more aromatic or heteroaromatic moieties [moiety/ies (Ar′′′)] and, optionally, one or more hydroxy groups and b) a chain (B), said chain (B) comprising a (per)fluoropolyether chain [chain $(R_f)$] and one or more hydroxy groups with the proviso that at least one phosphorous atom of the central core is substituted with chain (A) and to mixtures of compounds (L). The invention further relates to methods for preparing compounds (L), to lubricant compositions comprising compounds (L) and to methods for lubricating magnetic recording media comprising applying a compound (L) or a lubricant compositions containing them to the surface of said medium.

10 Claims, No Drawings

CYCLOPHOSPHAZENE DERIVATIVES

CROSS REFERENCE TO RELATED APPLICATIONS

This application is a U.S. national stage entry under 35 U.S.C. § 371 of International Application No. PCT/EP2015/070427 filed Sep. 8, 2015, which claims priority from European application No. 14184247.6 filed Sep. 10, 2014. The entire contents of these applications are explicitly incorporated herein by this reference.

TECHNICAL FIELD

The present invention relates to (per)fluoropolyether cyclophosphazene derivatives for use as lubricants for sliding or moving parts of magnetic recording media (MRM).

BACKGROUND ART

Phosphazene derivatives for use in the lubrication of sliding or moving parts of MRM are known in the art.

Examples of cyclophosphazene derivatives for such use are those containing at least one phosphazene cyclic group and at least one fully or partially fluorinated polyoxyalkylene chain [herein after also referred to as (per)fluoropolyether or PFPE chain] bearing one or more hydroxy groups. The phosphazene cyclic group is highly stable from the thermal standpoint and further increases the stability of the PFPE chain; without being bound to theory, it is believed that the phosphazene ring acts as a Lewis base which counteracts the catalytic effect on thermal degradation of the PFPE chain due to the Lewis acids typically present as impurities in the MRM (KANG, H. J., et al. The use of cyclic phosphazene additives to enhance the performance of the head/disk interface. *Lubrication Engineering*. 1999, vol. 55(3), p. 22-27.)

Certain patent documents, including US 2002183211 (AKADA TAMIO ET AL) 12 May 2002, US 2008020171 A (MATSUMURA OIL RES CORP [JP]) 24 Jan. 2008, US 2008305975 A (SEAGATE TECHNOLOGY LLC [US]) 11 Dec. 2008, WO 2007/043450 (MATSUMURA OIL RES CORP [JP]) 19 Apr. 2007 and US 2012276417 (WD MEDIA SINGAPORE PTE LTD [US]) 27 Jan. 2011 disclose lubricants for MRM containing at least one phosphazene cyclic group bearing at least one optionally substituted phenoxy group and at least one hydroxy-substituted PFPE chain.

However, it has been observed that the optionally substituted phenoxy group on the phosphazene ring might reduce the mobility of the lubricant and decrease the durability of the MRM. Thus, it would be desirable to provide PFPE phosphazene derivatives for the lubrication of MRM that do not show this drawback.

US 2012251843 (SEAGATE TECHNOLOGY LLC [US]) 10 Apr. 2012 discloses, inter alia, a composition comprising a central core comprising a cyclic group, including a cyclotriphosphazene, and six arms extending from the central core, wherein each arm comprises a PFPE or a PFPE derivative. The PFPE derivative can be a PFPE chain having one or more terminal functional groups including: —$CH_2OH$, —$OCH_2CH_2OH$, —$CH_2CH(OH)CH_2OH$, —$CH_2CH(OH)CH_3$ and —$OCH_2CH_2CH_2OH$. The PFPE derivative can also have non-terminal functional groups including —$CH_2CH(OH)CH_2$—, —$CH(OH)CH(OH)CH_2$—, —$CH_2CH(OH)CH_2CH(OH)CH_2$—, —$CH(CH_2OH)$— and —$CH(OH)CH(OH)CH_2$—.

US 20090318664 A (SEAGATE TECHNOLOGY LLC) 24 Dec. 2009 discloses compounds comprising a backbone comprising a PFPE chain; one or more cyclophosphazene rings attached to or incorporated into the backbone; and at least two functional groups attached either to the backbone or to the cyclophosphazene ring or both. In particular, this document refers to compounds wherein the cyclophosphazene ring comprises alkoxy or aryloxy substituents.

US 2012/0219826 (SEAGATE TECHNOLOGY LLC) discloses composition for use in lubricating thin film storage media, the composition including one or more central cores, wherein each arm comprises phenol or piperonyl.

SUMMARY OF INVENTION

The present invention provides further phosphazene derivatives for use in the lubrication of MRM and a method for obtaining such derivatives.

In particular, in a first aspect, the invention relates to a phosphazene compound [compound (L)] comprising a phosphazene central core wherein each phosphorus atom of said core bears substituents independently selected from:

a) a chain (A), said chain (A) comprising a (per)fluoropolyether chain [chain ($R_f$)], one or more aromatic or heteroaromatic moieties and, optionally, one or more hydroxy groups and b) a chain (B), said chain (B) comprising a (per)fluoropolyether chain [chain ($R_f$)] and one or more hydroxy groups with the proviso that at least one phosphorous atom of the central core is substituted with chain (A)

The invention also relates to mixtures of compounds (L).

Without being bound to theory, it is believed that the presence of said one or more aromatic or heteroaromatic moieties provides an optimum balance between the lubricant's adhesion to the underlying carbon surface and the lubricant's mobility, which results in increased durability of the MRM.

In a second aspect, the invention provides a method for manufacturing a compound (L) and mixtures thereof.

In a third aspect, the invention relates to a method of lubricating sliding or moving parts of MRM (including heat-assisted magnetic recording media, HAMR) comprising applying to such parts a compound (L) or a mixture thereof.

In a fourth aspect, the present invention relates to a lubricant composition [composition (C)] comprising a compound (L) or a mixture thereof and further ingredients.

In a fifth aspect, the present invention relates to a method of manufacturing a composition (C).

In a sixth aspect, the present invention relates to a MRM or HAMR comprising a compound (L) or a mixture thereof or a composition (C).

General Definitions

In the present description, when ranges are indicated, range extremes are included, unless indicated otherwise.

The acronym "PFPE" stands for "(per)fluoropolyether" and, when used as substantive, is intended to mean either the singular or the plural form, depending on the context. The prefix "(per)" in the term "(per)fluoropolyether" means that the polyether can be fully or partially fluorinated.

The term "haloalkyl" denotes a hydrocarbon group or compound wherein one or more hydrogen(s) is/are replaced with one or more halogen(s). The prefix "(per)" in the term "(per)haloalkyl" means that part or all of the hydrogen atoms can be replaced with halogen atoms.

Unless indicated otherwise, "halogen" or "halo" includes fluorine, chlorine, bromine and iodine.

The use of parentheses around symbols or numbers identifying the formulae, for example in expressions like "chain $(R_f)$", "chain (A)", "chain (B)", etc. . . . , has the mere purpose of better distinguishing the symbol or number from the rest of the text; thus, said parentheses could also be omitted.

Chain $(R_f)$ in chains (A) and (B) according to the present invention is a fully or partially fluorinated polyoxyalkylene chain that comprises, preferably consists of, repeating units R°, said repeating units being independently selected from the group consisting of:

(i) —CFXO—, wherein X is F or $CF_3$, (ii) —CFXCFXO—, wherein X, equal or different at each occurrence, is F or $CF_3$, with the proviso that at least one of X is —F, (iii) —$CF_2CF_2CW_2O$—, wherein each of W, equal or different from each other, are F, Cl, H, (iv) —$CF_2CF_2CF_2CF_2O$—, (v) —$(CF_2)_j$—CFZ—O— wherein j is an integer from 0 to 3 and Z is a group of general formula —$OR_f'T$, wherein $R_f'$ is a fluoropolyoxyalkene chain comprising a number of repeating units from 0 to 10, said recurring units being chosen among the followings: —CFXO—, —$CF_2CFXO$—, —$CF_2CF_2CF_2O$—, —$CF_2CF_2CF_2CF_2O$—, with each of each of X being independently F or $CF_3$ and T being a $C_1$-$C_3$ perfluoroalkyl group.

Preferably, chain $(R_f)$ complies with the following formula:

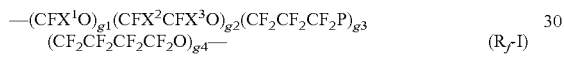
—$(CFX^1O)_{g1}(CFX^2CFX^3O)_{g2}(CF_2CF_2CF_2P)_{g3}$
$(CF_2CF_2CF_2CF_2O)_{g4}$— ($R_f$-I)

wherein:

$X^1$ is independently selected from —F and —$CF_3$, $X^2$, $X^3$, equal or different from each other and at each occurrence, are independently —F, —$CF_3$, with the proviso that at least one of X is —F;

g1, g2, g3, and g4, equal or different from each other, are independently integers ≥0, such that g1+g2+g3+g4 is in the range from 2 to 300, preferably from 2 to 100; should at least two of g1, g2, g3 and g4 be different from zero, the different recurring units are generally statistically distributed along the chain.

More preferably, chain $(R_f)$ is selected from chains of formula:

—$(CF_2CF_2O)_{a1}(CF_2O)_{a2}$— ($R_f$-IIA)

wherein:

a1 and a2 are independently integers ≥0 such that the number average molecular weight is between 400 and 10,000, preferably between 400 and 5,000; both a1 and a2 are preferably different from zero, with the ratio a1/a2 being preferably comprised between 0.1 and 10;

—$(CF_2CF_2O)_{b1}(CF_2O)_{b2}(CF(CF_3)O)_{b3}(CF_2CF(CF_3)$
$O)_{b4}$— ($R_f$-IIB)

wherein:

b1, b2, b3, b4, are independently integers ≥0 such that the number average molecular weight is between 400 and 10,000, preferably between 400 and 5,000; preferably b1 is 0, b2, b3, b4 are >0, with the ratio b4/(b2+b3) being ≥1;

—$(CF_2CF_2O)_{c1}(CF_2O)_{c2}(CF_2(CF_2)_{cw}CF_2O)_{c3}$— ($R_f$-IIC)

wherein:

cw=1 or 2;

c1, c2, and c3 are independently integers ≥0 chosen so that the number average molecular weight is between 400 and 10,000, preferably between 400 and 5,000; preferably c1, c2 and c3 are all >0, with the ratio c3/(c1+c2) being generally lower than 0.2;

—$(CF_2CF(CF_3)O)_d$— ($R_f$-IID)

wherein:

d is an integer >0 such that the number average molecular weight is between 400 and 10,000, preferably between 400 and 5,000;

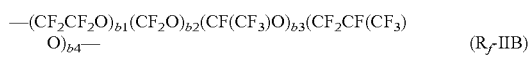
—$(CF_2CF_2C(Hal^*)_2O)_{e1}$—$(CF_2CF_2CH_2O)_{e2}$—
$(CF_2CF_2CH(Hal^*)O)_{e3}$— ($R_f$-IIE)

wherein:

Hal*, equal or different at each occurrence, is a halogen selected from fluorine and chlorine atoms, preferably a fluorine atom;

e1, e2, and e3, equal to or different from each other, are independently integers ≥0 such that the (e1+e2+e3) sum is comprised between 2 and 300.

Still more preferably, chain $(R_f)$ complies with formula ($R_f$-III) here below:

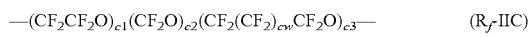
—$(CF_2CF_2O)_{a1}(CF_2O)_{a2}$— ($R_f$-III)

wherein:

a1, and a2 are integers >0 such that the number average molecular weight is between 400 and 10,000, preferably between 400 and 5,000, with the ratio a2/a1 being generally comprised between 0.1 and 10, more preferably between 0.2 and 5.

Typically, chain $(R_f)$ in chains (A) and (B) has two chain ends, one of them bearing a bridging group [group (G)] that connects chain $(R_f)$ to one phosphorus atom of the cyclophosphazene ring, as explained in detail below, and the other one bearing a free end group [group (E)]. In chain (A), the one or more aromatic or heteroaromatic moiety can be comprised either in group (G) or in group (E) or both, each of said groups optionally further comprising one or more hydroxy groups; preferably, the one or more aromatic or heteroaromatic moiety is comprised in group (E). In chain (B), the one or more hydroxy groups can be comprised either in group (G) or (E) or both; preferably, the one or more hydroxy group is comprised in group (E) or both in group (E) and in group (G).

Compounds (L)

Compounds (L) according to the present invention comprise a cyclophosphazene central core wherein each phosphorus atom of said core bears substituents independently selected from:

a) a chain (A), said chain (A) comprising a (per)fluoropolyether chain [chain $(R_f)$], one or more aromatic or heteroaromatic moieties [moiety/ies $(Ar^m)$] and, optionally, one or more hydroxy groups and b) a chain (B), said chain (B) comprising a (per)fluoropolyether chain [chain $(R_f)$] and one or more hydroxy groups with the proviso that at least one phosphorous atom of the central core is substituted with chain (A).

The phosphazene core is preferably selected from a cyclotriphosphazene core and a cyclotetraphosphazene core; more preferably, the cyclophosphazene core is a cyclotriphosphazene core.

Aromatic moiety $(Ar^m)$ is typically an aromatic ring comprising from 6 to 10 carbon atoms, said ring being optionally bound to or condensed with one or more further aromatic rings. Preferred aromatic rings are phenyl, naphthyl and biphenyl. According to one embodiment, the aromatic moiety is a phenyl moiety.

Heteroaromatic moiety (Ar$'''$) is typically a 5- to 10-membered heteroaromatic ring comprising at least one heteroatom independently selected from N, O and S, said ring being optionally bound to or condensed with one or more aromatic or heteroaromatic rings as defined above. According to a preferred embodiment of the invention, the heteroaromatic moiety is a pyridyl moiety.

The aromatic or heteroaromatic moiety can also be optionally condensed with a saturated or partially saturated 5- to 6-membered ring, said ring optionally comprising one or more heteroatoms independently selected from N, O and S.

The aromatic or heteroaromatic moiety is optionally substituted, i.e. it can also bear one or more substituents [substituent(s) (S)] independently selected from:
- straight or branched (per)haloalkyl groups, preferably $C_1$-$C_5$ (per)haloalkyl groups, more preferably $C_1$-$C_5$-perfluoroalkyl groups;
- halogens, preferably fluorine; and
- nitro groups.

Preferred substituents are independently selected from fluorine, trifluoromethyl and nitro.

Compounds (L) can be schematically depicted with general formula (L-1) below:

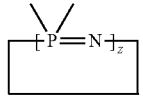

(L-1)

wherein:
x and y are 0, 1 or 2, with the proviso that x+y=2
z is an integer of at least 3 and
chains (A) and (B) are as defined above
and with the proviso that at least one chain (A) is present in formula (L-1).

Preferably, z ranges from 3 to 7 and is preferably selected from 3 and 4; more preferably z is 3.

Compounds (L) can be in the form of mixtures typically comprising compounds (L) differing from one another in the number and/or kind of chains (A) and (B) on each cyclophosphazene ring. Mixtures of compounds (L) may also comprise compounds (L) differing from one another in the kind of cyclophosphazene ring.

Compounds (L) may also be in admixture with compounds that also contain one or more chain (B'), said chain (B') comprising a chain ($R_f$) as defined above, wherein both ends of chain ($R_f$) are bound either to a same phosphorus atom of the cyclophosphazene ring or to two different phosphorus atoms of the cyclophosphazene ring via a bridging group (G) comprising one or more aromatic or heteroatomatic moieties and/or one or more hydroxy groups, as defined in detail below. The former compounds will be herein after referred to as "spiro-compounds", while the latter will be herein after referred to as "ansa-compounds". In other words, spiro- and ansa-compounds comprise a cyclophosphazene central core wherein each phosphorus atom of said core bears substituents independently selected from:

a) a chain (A), said chain (A) comprising a (per)fluoropolyether chain [chain ($R_f$)], one or more aromatic or heteroaromatic moieties [moiety/ies (Ar$'''$)] and, optionally, one or more hydroxy groups and b) a chain (B), said chain (B) comprising a (per)fluoropolyether chain [chain ($R_f$)] and one or more hydroxy groups and c) at least one chain (B'), said chain (B') comprising a (per)fluoropolyether chain ($R_f$), wherein both ends of chain ($R_f$) are bound either to a same phosphorus atom of the cyclophosphazene ring or to two different phosphorus atoms of the cyclophosphazene ring via a bridging group (G), said group (G) comprising one or more aromatic or heteroatomatic moieties and/or one or more hydroxy groups, with the proviso that at least one chain (A) or at least one chain (B') wherein bridging group (G) comprises one or more aromatic or heteroaromatic moieties (Ar$'''$) is present.

Typically, spiro-compounds can be schematically represented with the following formula:

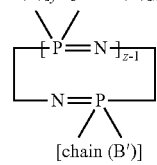

spiro (L-1)

wherein x, y and z, chains (A), (B) and (B') are as defined above with the proviso that at least one chain (A) or at least one chain (B') wherein bridging group (G) comprises one or more aromatic or heteroaromatic moieties (Ar$'''$) is present.

Typically, ansa compounds can be schematically represented with the following formula:

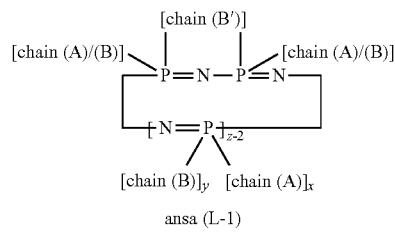

ansa (L-1)

wherein x, y and z, chains (A), (B) and (B') are as defined above and chain (A)/(B) indicates that either chain (A) or chain (B) can be bound to the phosphorus atom with the proviso that at least one chain (A) or at least one chain (B') wherein bridging group (G) comprises one or more aromatic or heteroaromatic moieties (Ar$'''$) is present.

Preferably, chain (A) complies with formula (A-1) below:

-G*-O—$R_f$-E*       (A-1)

wherein:
G* is a divalent bridging group, partially fluorinated and containing one or more oxygen atoms, said group optionally comprising one or more hydroxy groups;
$R_f$ is as defined above; and
E* represents a hydrocarbon group, partially fluorinated and containing one or more oxygen atoms, said group optionally comprising one or more hydroxy groups
and wherein either (G*) or (E*) comprises the one or more aromatic or heteroaromatic moiety (Ar$'''$). Preferably, moiety (Ar$'''$) is comprised in group (E*).

Preferred examples of groups (G*) comply with formulae (i*)-(vii*) below:

—(OCH$_2$CH$_2$)$_n$OCH$_2$XFC—; (i*)

—[OCH(CH$_3$)CH$_2$)]$_n$OCH$_2$XFC—; (ii*)

—(OCH$_2$CH$_2$)$_n$OCH$_2$CF$_2$CF$_2$—; (iii*)

—[OCH$_2$CH(OH)CH$_2$]$_{n'}$OCH$_2$XFC—; (iv*)

—[OCH(CH$_2$OH)CH$_2$]$_{n'}$OCH$_2$XFC—; (v*)

—[OCH$_2$CH(OH)CH$_2$)$_{n'}$OCH$_2$CF$_2$CF$_2$—; and (vi*)

—[OCH(CH$_2$OH)CH$_2$]$_{n'}$OCH$_2$CF$_2$CF$_2$—, wherein: (vii*)

X is F or CF$_3$, n ranges from 0 to 5 and n' ranges from 1 to 3, being understood that the oxygen atom on the left-hand side of formulae (i*)-(vii*) is bound to a phosphorous atom of the cyclophosphazene core and the —CFX— or —CF$_2$— group on the right-hand side is bound to the oxygen atom of the —O—R$_f$— moiety.

Preferably, bridging group (G*) complies with:
formula (i*) wherein X is F and n is selected from 0, 1 and 2; in one preferred embodiment, n is 0; or
with formula (iv*) wherein X is F and n' is 1.

Preferred examples of groups (E*) comply with formulae (viii*)-(xii*) below:

—CFXCH$_2$O(CH$_2$CH$_2$O)$_n$(CH$_2$)$_p$Ar'''; (viii*)

—CFXCH$_2$O[CH$_2$CH(CH$_3$)O]$_n$(CH$_2$)$_p$Ar'''; (ix*)

—CF$_2$CF$_2$CH$_2$O(CH$_2$CH$_2$O)$_n$(CH$_2$)$_p$Ar'''; (x*)

—CFXCH$_2$O[CH$_2$CH(OH)CH$_2$O]$_{n'}$(CH$_2$)$_p$Ar''' and (xi*)

—CF$_2$CF$_2$CH$_2$O[CH$_2$CH(OH)CH$_2$O]$_{n'}$(CH$_2$)$_p$Ar''', wherein: (xii*)

X is F or CF$_3$, n and n' and Ar''' are as defined above and p is 0 or 1.

Preferably, group (E*) complies with:
formula (viii*) wherein X is F, n is selected from 0, 1 and 2 and p is 0; according to one preferred embodiment, n is 0; or
with formula (xi*) wherein X is F, n' is 1 and p is 0.

Preferably, in groups (E*), (Ar''') is selected from phenyl or pyridyl, preferably bearing one or more substituents as defined above, more preferably independently selected from fluorine, trifluoromethyl and nitro.

Preferably, chain (B) complies with formula (B-1) below:

-G-O—R$_f$-E (B-1)

wherein:
G** is a divalent bridging group, partially fluorinated and containing one or more oxygen atoms, said group optionally comprising one or more hydroxy groups;
R$_f$ is as defined above and
E** represents a hydrocarbon group, partially fluorinated and optionally containing one or more oxygen atoms, said group comprising one or more hydroxy groups.

Preferred examples of groups (G**) comply with formulae (i*)-(vii*) indicated above for group (G*).

Preferred examples of groups (E) comply with formulae (viii)-(xii**) below:

—CFXCH$_2$O(CH$_2$CH$_2$O)$_n$H; (viii**)

—CFXCH$_2$O[CH$_2$CH(CH$_3$)O]$_n$H; (ix**)

—CF$_2$CF$_2$CH$_2$O(CH$_2$CH$_2$O)$_n$H; (x**)

—CFXCH$_2$O[CH$_2$CH(OH)CH$_2$O]$_{n'}$H and (xi**)

—CF$_2$CF$_2$CH$_2$O[CH$_2$CH(OH)CH$_2$O]$_{n'}$H, (xii**)

wherein:
X is F or CF$_3$ and n and n' are as defined above.

Preferably, group (E**) complies with:
formula (viii**) wherein X is F and n is selected from 0, 1 and 2; more preferably, n is 0 or
formula (xi**) wherein X is F and n' is 1.

Preferably, chain (B') complies with formula (B'-1) below:

-G-O—R$_f$-G*- (B'-1)

in which (G) is as defined above and (G*) is selected from formulae (i*)-(vii*) below:

—CFXCH$_2$O(CH$_2$CH$_2$O)$_n$—; (i***)

—CFXCH$_2$O[CH$_2$CH(CH$_3$)O]$_n$—; (ii***)

—CF$_2$CF$_2$CH$_2$O(CH$_2$CH$_2$)$_n$—; (iii***)

—CFXCH$_2$O[CH$_2$CH(OH)CH$_2$O]$_{n'}$—; (iv***)

—CFXCH$_2$O[CH$_2$CH(CH$_2$OH)O]$_{n'}$—; (v***)

—CF$_2$CF$_2$CH$_2$O[CH$_2$CH(OH)CH$_2$O]$_{n'}$— and (vi***)

—CF$_2$CF$_2$CH$_2$O[CH$_2$CH(CH$_2$OH)O]$_{n'}$— (vii***)

wherein X is F or CF$_3$, n ranges from 0 to 5 and n' ranges from 1 to 3, being understood that, in group (G*), the —CFX— or —CF$_2$— group on the left-hand side is bound to (R$_f$) and the oxygen atom on the right-hand side of formulae (i*)-(vii***) is bound to a phosphorus atom of the cyclophosphazene moiety.

Preferably, in chains (A-1), (B-1) and (B'-1), (R$_f$) complies with formula (R$_f$-I), more preferably with formulae (R$_f$-IIA)-(R$_f$-IIE), still more preferably with formula (R$_f$-III) as defined above.

A particularly preferred group of compounds (L) comprises a cyclotriphosphazene central core and chains (A-1) and (B-1) as defined above. This group of compounds complies with formula (L-2) below:

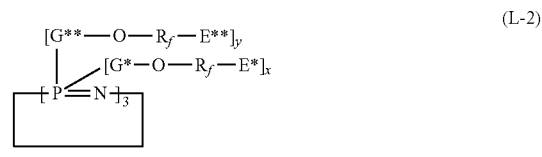

(L-2)

wherein (G*), (E*), (G) and (E), x and y are as defined above.

Compounds (L-2) may also be in admixture with spiro compounds and/or ansa compounds typically represented by formulae spiro (L-2) and ansa (L-2) below:

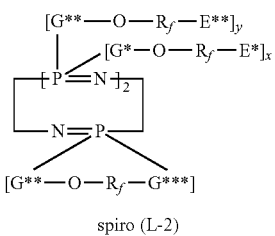

spiro (L-2)

-continued

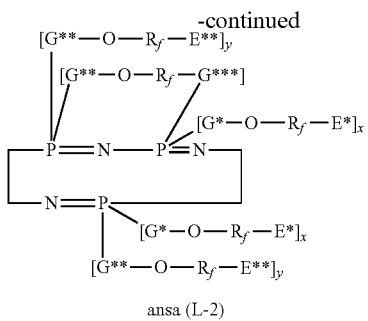

ansa (L-2)

wherein (G*), (E*), (G), (G*) and (E**), (R$_f$), x and y are as defined above.

Preferred compounds (L-2) and the corresponding spiro (L-2) and ansa (L-2) compounds are those wherein:
(R$_f$) complies with formula (R$_f$-III) as defined above;
groups (G*) and (G**) comply with formula (i*) wherein X is F and n is selected from 0, 1 and 2; in a preferred embodiment, n is 0;
group (G*) complies with formula (i*) wherein X is F and n is selected from 0, 1 and 2; in a preferred embodiment, n is 0;
group E* complies with formula (viii*) as defined above wherein X is F, n is selected from 0, 1 and 2 and p is 0; and (Ar''') is an optionally substituted phenyl or pyridyl group; in a preferred embodiment, n is 0;
group (E) complies with formula (viii) wherein X is F, n is selected from 0, 1 and 2; in a preferred embodiment, n is 0.

Method for the Manufacture of Compounds (L)

The present invention further comprises methods for preparing compounds (L).

Compounds (L) according to the present invention can be conveniently prepared with a method which comprises the reaction of a perhalocyclophosphazene with:
a PFPE alcohol comprising a (per)fluoropolyether chain (R$_f$) as defined above, said chain having two chain ends, wherein one chain end comprises at least one hydroxy group and, optionally, one or more aromatic or heteroaromatic moieties (Ar'''), and the other chain end comprises one or more aromatic or heteroaromatic moieties (Ar''') and, optionally, one or more hydroxy groups [herein after "Ar-PFPE-OH" ] and, optionally,
a PFPE polyol comprising a (per)fluoropolyether chain (R$_f$) as defined above, said chain having two chain ends, wherein each chain end comprises at least one hydroxy group (herein after "PFPE-Pol").

Typically, the method comprises the reaction of a perhalocyclophosphazene with a mixture comprising both Ar-PFPE-OH and PFPE-Pol [herein after mixture (M-1)].

Perhalocyclophosphazenes suitable for carrying out the process of the invention comply with formula (CP-1) here below:

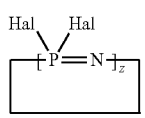 (CP-1)

wherein Hal represents a halogen selected from fluorine, chlorine, bromine and iodine, preferably chlorine, and z is an integer equal to or higher than 3, preferably ranging from 3 to 7. Preferably, perhalocyclophosphazenes are selected from those of formula (CP-1A) or (CP-1B) here below:

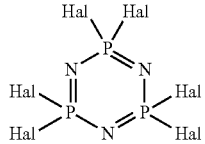 (CP-1A)

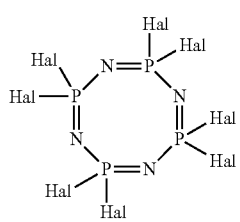 (CP-1B)

wherein Hal is as defined above. Preferably, Hal is chlorine.

In the process of the invention, it is also possible to use mixtures of more perhalocyclophosphazenes, in particular mixtures of (CP-1A) and (CP-1B) as defined above. However, it is preferred to use only one perhalocyclophosphazene; particularly preferred is the use of a perhalocyclophosphazene of formula (CP-1A); more preferably, (CP-1A) is hexachlorocyclophosphazene.

Perhalocyclophosphazenes (CP-1A) and (CP-1B) are commercially available and can be obtained, for example, from Strem Chemicals, Inc.

According to a preferred embodiment, the method comprises the following steps:
(a) providing a mixture (M-1) as defined above;
(b) reacting mixture (M-1) with a perhalocyclophosphazene compound (CP-1) as defined above to provide a mixture (M-2);
(c) optionally submitting mixture (M-2) to purification passages.

Typically, step (a) comprises the nucleophile reaction of a PFPE-Pol with a substituted aromatic or heteroaromatic compound [compound (Ar)], i.e. an aromatic or heteroaromatic compound bearing at least one group able to undergo nucleophilic substitution.

Preferred PFPE-Pol comply with general formula (Pol-I):

 (Pol-I)

wherein (R$_f$) is a fluoropolyoxyalkylene chain as defined above and Y represents a hydrocarbon group containing at least one hydroxy group, said hydrocarbon group being partially fluorinated and optionally containing one or more oxygen atoms.

Preferred examples of (Pol-I) are those wherein groups Y, equal to or different from one another, are selected from formulae (viii)-(xii) indicated above for groups (E**).

Preferably, chain (R$_f$) complies with formula (R$_f$-III) above.

In one preferred embodiment of (Pol-I) [herein after (Pol-I$^a$)], chain (R$_f$) complies with formula (R$_f$-III) above and both groups Y comply with formula (viii**) wherein X is F and n is selected from 0, 1 and 2; preferably, n is 0. (Pol-I$^a$) are commercially available from Solvay Specialty Polymers Italy or can be obtained by multiple distillation and purification of such products in order to properly increase their —OH functionality and narrow their molecular weight distribution (i.e. reduce their polydispersity index Mw/Mn) around the desired average molecular weight.

In another preferred embodiment of (Pol-I) [herein after (Pol-$I^b$)], chain ($R_f$) complies with formula ($R_f$-III) above, one group Y complies with formula (viii) wherein X is F and n is 0 and the other one complies with formula (xi) wherein X is F and n' is 1.

In another preferred embodiment of (Pol-I) [herein after (Pol-$I^c$)], chain ($R_f$) complies with formula ($R_f$-III) above and both groups Y comply with formula (xi**) wherein X is F and n' is 1.

Polyols (Pol-$I^c$) can be prepared from polyols (Pol-$I^a$) wherein n is 0 through a process comprising the reaction of a (Pol-$I^a$) with glycerine of formula:

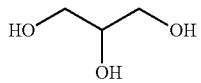

in an activated and protected form (activated protected glycerine="APG"), followed by removal of the protective groups, as disclosed in EP 2197939 A (SOLVAY SOLEXIS S.P.A.) 23 Jun. 2010, which is herein incorporated by reference. Protective groups and activating groups disclosed in EP 2197939 are preferred for the purposes of the present invention.

The procedure disclosed in EP 2197939 allows also to conveniently manufacture mixtures of PFPE (Pol-$I^a$) wherein n is 0, (Pol-$I^b$) and (Pol-$I^c$) that can be used as such in step (a) according to the present invention, thereby finally providing compounds (L) with different kind of chains (A) and (B). Such mixtures can be obtained if the reaction between a (Pol-$I^a$) wherein n is 0 and APG is not allowed to proceed until 100% conversion of the hydroxy end groups of (Pol-$I^a$) wherein n is 0 into the corresponding protected diol end groups. In particular, following the procedure of example 1 of EP 2197939, which comprises the reaction of the mesyl derivative of Solketal [(2,2-dimethyl-1,3-dioxo-lan-4-yl)methanol] with a PFPE (Pol-$I^a$) wherein n is 0 and by allowing the reaction to proceed until conversion lower than 100%, a mixture containing:

unreacted (Pol-$I^a$) wherein n is 0;
(Pol-$I^b$) wherein the two vicinal hydroxy groups in group Y, which comply with formula (xi**) wherein X is F and n' is 1, are protected with an isopropylidene ketal and
(Pol-$I^c$) wherein the two vicinal hydroxy groups in both groups Y are protected with an isopropylidene ketal.

A mixture of (Pol-$I^a$) wherein n is 0, (Pol-$I^b$) and (Pol-$I^c$) wherein (Pol-$I^b$) and (Pol-$I^c$) are protected can be used as such in step (a) and removal of the protections can be carried out at the end of step (a) or at the end of step (b).

Typically, substituted aromatic compounds (Ar) for use in the manufacture of mixture (M-1) are selected from those comprising an aromatic ring having from 6 to 10 carbon atoms, said ring being optionally bound to or condensed with one or more further aromatic rings. Preferred aromatic compounds are substituted benzene, naphthalene and biphenyl. More preferably, the substituted aromatic compound is a substituted benzene.

Typically, substituted heteroaromatic compounds (Ar) comprise 5- to 10-membered heteroaromatic ring comprising at least one heteroatom selected from N, O, and S, said ring being optionally bound to or condensed with one or more aromatic or heteroaromatic ring as defined above.

According to a preferred embodiment of the invention, the substituted heteroaromatic compound (Ar) is a substituted pyridine.

The substituted aromatic or heteroaromatic compound (Ar) can also be optionally condensed with a saturated or partially saturated 5- to 6-membered ring, said ring optionally comprising one or more heteroatoms independently selected from N, O and S.

"Substituted aromatic or heteroaromatic" means that compounds (Ar) bear one substituent [substituent (S')] susceptible to undergo nucleophilic substitution; typically, substituent (S') is a halogen, preferably chlorine, or a straight or branched alkyl chain bearing at least one substituent able to undergo nucleophilic substitution, preferably $C_1$-$C_5$haloalkyl, more preferably chloromethyl.

Compound (Ar) can also be optionally substituted with one or more further substituents [substituent (S)] independently selected from those indicated above in respect of moiety ($Ar'''$). In particular, one or more such further substituents (S) are present if substituent (S') is a halogen. Preferred further substituents (S) are fluorine, trifluoromethyl and nitro.

Preferred examples of substituted aromatic and heteroaromatic compounds (Ar) are 2-chloro-2,4-dinitrobenzene and 2-chloro-5(trifluoromethyl)pyridine.

For the purposes of the preparation of mixture (M-1), the reaction of the PFPE-Pol with compound (Ar) is carried out in the presence of a base, such as a carbonate, a ter-butylate or a hydroxide. Typically, one or more PFPE-Pol and a compound (Ar) are combined with the selected base and heated at a temperature ranging from 60° C. to 90° C. If more hydroxy groups are present at one end of a PFPE-Pol, such groups can also be protected, for example as explained above with reference to mixtures of (Pol-$I^a$)-(Pol-$I^c$). The presence of a base allows obtaining the corresponding salified PFPE-Pol which acts as the nucleophile species reacting with compound (Ar) to provide the corresponding Ar-PFPE-OH. The amount of PFPE-Pol, base and compound (Ar) will be determined by the skilled person on a case by case basis according to desired conversion percentage into Ar-PFPE-OH. Usually the PFPE-Pol, optionally in the protected form, is used in such an amount as the equivalents of free hydroxy groups are in excess with respect to the equivalents of base, while compound (Ar) is used in an amount typically ranging from 1:1 to 2:1 with respect to the equivalents of base.

Upon completion of the reaction between PFPE-Pol and compound (Ar), the resulting mixture (M-1) is cooled to room temperature, neutralized with a mineral acid, typically HCl, and, after phase separation, residual solvents are removed by distillation under reduced pressure. If PFPE-Pol is used in a protected form, the protections can be removed.

Typically, mixture (M-1) obtained in step (a) comprises compounds complying with formula:

$$Y\text{—}O\text{—}R_f\text{—}Z \qquad (M\text{-}1)$$

wherein Y is as defined above, while Z is a group Y as defined above or is a partially fluorinated hydrocarbon group comprising one or more oxygen atoms, said group comprising aromatic moiety ($Ar'''$) and, optionally, one or more hydroxy groups. Preferably, when Z is other than Y, it complies with formulae (viii*)-(xii*) reported above for group (E*).

Preferred mixtures (M-1) are those obtainable by reaction of a (Pol-$I^a$) and those obtained by reaction of a mixture of (Pol-$I^a$) wherein n is 0, (Pol-$I^b$) and (Pol-$I^c$), optionally in the protected form, with a substituted aromatic or heteroaromatic compound (Ar), preferably with a substituted benzene or a substituted pyridine.

Mixture (M-1) can be submitted to purification in order to increase the amount of alcohol Ar-PFPE-OH and reduce, or completely remove, the amount of PFPE-Pol, or can be used as such in step (b), i.e. in the reaction with a perhalocyclophosphazene. This reaction is typically carried out in the presence of a base, usually selected from those indicated above for the preparation of mixture (M-1). Typically, mixture (M-1) is contacted with a solution of a base and heated under reduced pressure until complete elimination of water. Usually, the temperature ranges from 70 to 80° C. Usually, if mixture (M-1) still comprises a PFPE-Pol or comprises Ar-PFPE-OH with free hydroxy groups at both ends of the PFPE chain, the amount of base will be selected in such a way as to minimize the amount of salified hydroxy groups at both ends of the PFPE chain. In this way, the formation of spiro- and ansa-products and also the formation of by-products resulting from the reaction of said salified groups with two different perhalocyclophosphazenes (said by-products will be herein after defined as "bridged" by-products) can be reduced. Appropriate temperatures can be selected by the skilled person according to the selected base and mixture (M-1). The resulting mixture is then contacted with a solution of perhalocyclophosphazene in an appropriate solvent, which is typically selected from hydrofluoroethers (HFEs), like 3M™ Novec™ HFEs, hydrofluorocarbons (HFCs) and hexafluoroxylene, the preferred solvent being hexafluoroxylene. The kind and amount of solvent will be selected by the skilled person according to the selected perhalocyclophosphazene; however, the amount of solvent is typically adjusted in such a way as the concentration of perhalocyclophosphazene ranges from 1 to 10% w/w.

Thereafter, the reaction mixture is allowed to react at a temperature typically ranging from 70° C. to 90° C. until $^{31}$P-NMR reveals complete disappearance of the P-Hal groups, typically the conversion of the P-Hal groups into P—OCH$_2$— groups. This conversion is revealed by the appearance of a singlet at 17 ppm.

At the end of the reaction, the reaction mixture is cooled to room temperature, neutralized with a mineral acid, typically HCl, and then, after phase separation, any residual solvents are removed by distillation under reduced pressure.

The resulting reaction product typically comprises a compound (L) represented by formula (L-1) as defined above, an excess of unreacted mixture (M-1), spiro- and ansa-compounds and bridged by-products. This mixture will be herein after referred to as "mixture (M-2)". When a hexahalocyclophosphazene is used, like hexachlorocyclotriphosphazene, a mixture (M-2) can be obtained wherein compound (L) is a compound (L-2) as defined above and any spiro- and ansa-compounds comply with formulae spiro (L-2) and ansa (L-2). If prior to step (b) (M-1) is purified in such a way as to completely remove any unreacted PFPE-Pol and no Ar-PFPE-OH with free hydroxy groups at both ends of the PFPE chain is present in mixture (M-1), no spiro- and ansa-compounds or bridged by-product will be comprised in the reaction product and compound (L) will comprise only chains (A).

Mixture (M-2) can then be submitted to one or more purification steps [steps (c)] in order to separate compounds (L) from unreacted mixture (M-1), spiro- and ansa-compounds and bridged-by-products.

Typically, mixture (M-2) is submitted to purification with chromatographic techniques or to fractionation with supercritical carbon dioxide (scCO$_2$); by means of this technique, unreacted mixture (M-1) is removed at low pressure, while bridged-by-products are removed at high pressure. Intermediate fractions comprise compounds (L) and spiro- and ansa-compounds. Among the intermediate fractions, those which are eluted first contain a higher amount of spiro- and ansa-compounds, while those eluted last contain a higher amount of compounds (L). All intermediate fractions can be pooled together and used as such; otherwise, selected fractions can be pooled together and submitted again to fractionation with scCO$_2$ or to chromatographic techniques in order to further separate spiro- and ansa-compounds from compounds (L). This process can be repeated as many times as desired in order to increase the purity of compounds (L) according to the intended use.

Compositions Comprising Compounds (L) and Methods Comprising their Use

Compounds (L) and mixtures thereof can be used as lubricants for sliding or moving parts of MRM, including those of media used in heat-assisted magnetic recording (HAMR).

Compounds (L) or mixtures thereof can also be used in admixture with their corresponding spiro- and ansa-compounds.

Thus, a further object of the present invention is a method of lubricating sliding or moving parts of MRM (including those for HAMR), said method comprising applying to said parts compounds (L) or mixtures thereof, optionally in admixture with their corresponding spiro- and ansa-compounds.

Compounds (L) or mixtures thereof, optionally in admixture with their corresponding spiro- and ansa compounds, can also be used in admixture with one or more lubricants typically used in compositions for lubricating MRM, including MRM for HAMR. Examples of such lubricants such as Fomblin® Z DOL PFPE, Fomblin® Z Tetraol 2000S PFPE, Fomblin® Z Tetraol GT PFPE.

Accordingly, the present invention relates to a lubricant composition [composition (C)] comprising one or more compounds (L), optionally in admixture with the corresponding spiro- and ansa-compounds, and one or more lubricants and to a method for the manufacture of a composition (C), said method comprising mixing one or more compounds (L), optionally in admixture with the corresponding spiro- and ansa compounds, with one or more lubricants.

A further object of the present invention is a MRM, including media for HAMR, comprising a sliding or moving part having applied thereto one or more compounds (L) or a composition (C).

Should the disclosure of ant patents, patent applications and publications which are incorporated herein by reference conflict with the description of the present application to the extent that it may render a term unclear, the present description shall take precedence.

The invention will be herein after illustrated in greater detail by means of the Examples contained in the following Experimental Section; the Examples are merely illustrative and are by no means to be interpreted as limiting the scope of the invention.

EXPERIMENTAL SECTION

Materials

The PFPE-Pol used in Examples 1 and 2 was obtained by multiple distillation and purification of commercially available products from Solvay Specialty Polymers Italy.

2-chloro-5-(trifluoromethyl)pyridine, 2-chloro-2,4-dinitrobenzene, potassium tert-butoxide, tert-butyl alcohol (TBA), HCl, KOH, isobutyl alcohol, potassium carbonate, tetramethylammonium hydroxide and acetonitrile were obtained from Sigma-Aldrich® and were used as received.

Hexachlocyclotriphosphazene (HCP) was purchased from Strem Chemicals, Inc.

1,3-hexafluoroxylene (HFX) was obtained from Miteni S.p.A. and was used as received.

Methods

NMR Spectroscopy $^{31}$P, $^{19}$F, $^{1}$H and $^{13}$C NMR spectra were recorded at 25° C. using an Agilent® System 500 operating at 121.40 MHz for $^{31}$P, 470.30 MHz for $^{19}$F, 499.86 MHz for $^{1}$H and 125.70 MHz for $^{13}$C. Samples have been acquired dissolved in a mixture 3:1 v/v CFC113/Methanol-$d_4$ (CD$_3$OD) 99.9 atom % D at about 10% w/w.

Definition and Determination of the Ratio R

R is defined as the ratio between =P—OCH$_2$— groups (P is the phosphorus atom in the cyclophosphazene ring) and the overall amount of free end groups.

The estimation of ratio R has been performed by using fluorine, proton and optionally carbon spectra which show distinct peaks for =POCH$_2$— and free end groups.

Gel Permeation Chromatography (GPC)

The molecular weight distribution and the polydispersity index (Mw/Mn) were determined by Gel Permeation Chromatography (GPC). The GPC system was equipped with a Waters HPLC 515 pump, three PL-Gel columns (one Mixed-D and two Mixed-E) and a Waters 2414 refractive index detector. The columns and detector were thermostated at 35° C. The mobile phase was a mixture of 1,3-bis (trifluoromethyl)benzene and isopropanol (80/20 vol.), fluxed at 1.0 ml/min. Samples were dissolved at 1% wt/vol concentration in the mobile phase under stirring at room temperature until complete dissolution (about 1 hour). For the analysis 200 μl of the solution were injected. The calibration curve was obtained by using eight Fomblin® Z DOL PFPE narrow fractions with molecular weights known from NMR analysis and falling in the range 461-6878. Acquisition and the calculations were performed using Waters Empower software.

Fractionation with Supercritical CO$_2$ (scCO$_2$)

Fractionation with scCO$_2$ was carried out using a 300 ml SFT-150 Supercritical CO$_2$ Extraction System.

Example 1

Step (a)—Preparation of a mixture (M-1) [reaction of a PFPE-Pol with 2-chloro-5-(trifluoromethyl)pyridine] (target conversion=10%)

1000.0 g of a PFPE-Pol of formula HO—CH$_2$CF$_2$O (CF$_2$CF$_2$O)$_{a1}$(CF$_2$O)$_{a2}$CF$_2$CH$_2$—OH (MW=925 g/mol, a1/a2=0.96, EW=464 g/eq; 2155 meq.) and 43.0 g of 2-chloro-5-(trifluoromethyl)pyridine of formula Cl(C$_5$H$_3$N)CF$_3$ (237 meq.) were charged into a 5 l round-bottomed flask equipped with mechanical stirrer, dropping funnel, thermometer and condenser. The resulting non-homogeneous mixture was placed under dry nitrogen and heated at 60° C. under stirring. In a separated flask, 25.4 g of potassium tert-butoxide (95%, 215 meq) was dissolved in 260 g of tert-butyl alcohol (TBA); the resulting clear solution was transferred via a double-ended needle into the dropping funnel and slowly added to the mixture of PFPE-Pol and 2-chloro-5-(trifluoromethyl)pyridine under stirring at 65° C. for 4.5 hours; after this time, precipitation of KCl was observed. After further 60 minutes under stirring at 65° C., a 10% conversion was achieved, as confirmed by $^{19}$F-NMR spectroscopy. After cooling, the mixture was washed four times with 4000 g distilled water and 20 g HCl 37% w/w water solution. Every time the resulting two phases were vigorously stirred at room temperature for a few minutes and, after separation, the lower organic layer was collected. The solvents (TBA and traces of water) were removed by distillation at 70° C. under reduced pressure (residual pressure=2 Pa) to afford 1016 g crude product with a hydroxyl equivalent weight EW=478.5 g/eq and having formula:

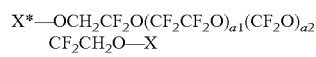
X*—OCH$_2$CF$_2$O(CF$_2$CF$_2$O)$_{a1}$(CF$_2$O)$_{a2}$CF$_2$CH$_2$O—X wherein X*=H (90% on molar basis) or X*=(C$_5$H$_3$N)CF$_3$ (10% on molar basis).

Step (b)—Preparation of a Mixture (M-2) from Mixture (M-1) and Hexachlorocyclophosphazene 1000.0 g of mixture (M-1) (EW=478.5 g/eq; 2090 meq.) obtained from step (a) were charged into a 5 l round-bottomed flask equipped with mechanical stirrer, dropping funnel, thermometer and condenser, and then added with 73 g KOH (554 meq.; 42.5% solution in water). The mixture was heated and maintained at 70° C. under stirring, then vacuum was applied to the flask by means of a mechanical pump until complete elimination of water (about 60 minutes at P=3 kPa), to obtain a homogeneous solution. In a separated flask, 14.6 g hexachlorocyclotriphosphazene (HCP, 252 meq.) was dissolved in 500 g 1,3-hexafluoroxylene (HFX); the resulting solution was transferred via a double-ended needle into the dropping funnel and slowly added to the solution of (M-1) and KOH, under stirring at 78° C., for 6.5 hours. The reaction mixture was maintained at 78° C. under stirring, monitoring the conversion from time to time by $^{31}$P-NMR analysis. After 60 minutes, conversion was quantitative (singlet in the $^{31}$P-NMR spectrum at 17 ppm) and the reaction was stopped. After cooling to room temperature, the mixture was added with 510 g distilled water, 45 g HCl 37% w/w water solution and 34 g isobutyl alcohol. The two phases were vigorously stirred and, after separation, the lower organic layer was collected. The procedure was repeated, using 425 g of distilled water instead of 510. After separation, the solvents (HFX and isobutyl alcohol) were removed by distillation at 70° C. under reduced pressure (P=2 Pa) to afford 958 g crude product which was submitted to thin-layer distillation so as to remove most of the excess of unreacted mixture (M-1). Through two passages at 120° C. (P=2 Pa) and 140° C. (P=0.6 Pa) two fractions (75% and 7% by weight, respectively) of only unreacted mixture (M-1), as confirmed by the absence of signals in the $^{31}$P-NMR spectrum, were removed, leaving 170 g of a high boiling, low volatility residue, which was characterized by $^{19}$F-NMR, $^{1}$H-NMR and $^{31}$P-NMR. The GPC chromatogram showed four main components having a peak molecular weight of 1280, 4550, 7550 and 10100 dalton respectively. The first component corresponds to residual unreacted mixture (M-1), the second component is attributed to the resulting compound (L-2) and the corresponding spiro (L-2) and ansa (L-2) compounds, while the last two components are most likely attributed to bridged by-products.

Step (c)—Fractionation of Mixture (M-2) with Supercritical Carbon Dioxide (scCO$_2$)

Mixture (M-2) obtained from step (b) was charged into a 300 ml SFT-150 Supercritical CO$_2$ Extraction System and heated at 100° C. Through a step-by-step pressure increase (from 19 to 50 MPa) and operating at a CO$_2$ flow rate of 4 Nl/min, compound (L-2) and the corresponding spiro (L-2)

and ansa (L-2) were isolated. Any residual unreacted mixture (M-1) was easily removed at scCO$_2$ low pressure, while bridged by-products were selectively collected at high pressure. Each fraction was characterized by $^{31}$P-NMR, $^{19}$F-NMR, $^{1}$H-NMR, $^{13}$C-NMR and GPC. Fractions containing only compound (L-2) and the corresponding spiro (L-2) and ansa (L-2) were pooled together (34.6% by weight). The ratio R between the P—OCH$_2$CF$_2$O— and the —OCF$_2$X end-groups (X=—CH$_2$OH, —CH$_2$O(C$_5$H$_3$N)CF$_3$, —F or —H, measured by $^{19}$F-NMR, $^{1}$H-NMR and $^{13}$C-NMR) was found to be 1.25, corresponding to a molar percent composition of 41% (L-2) and 59% spiro (L-2)+ansa (L-2). The molar ratio between —CH$_2$OH and —CH$_2$O(C$_5$H$_3$N)CF$_3$ end-groups resulted to be 8.27, corresponding to 0.51 —CH$_2$O(C$_5$H$_3$N)CF$_3$ end-groups per molecule.

Example 2

Step (a)—Preparation of a Mixture (M-1) [Reaction of a PFPE-Pol with 2-chloro-2,4-dinitrobenzene] (target conversion=31%)

600.0 g of PFPE-Pol of formula: HO—CH$_2$CF$_2$O(CF$_2$CF$_2$O)$_{a1}$(CF$_2$O)$_{a2}$CF$_2$CH$_2$—OH (MW=1027 g/mol, a1/a2=0.95, EW=515 g/eq; 1165.0 meq.), 73.4 g of 2-chloro-2,4-dinitrobenzene of formula ClC$_6$H$_3$(NO$_2$)$_2$ (362.4 meq.), 112.5 g of potassium carbonate (814 mmol), 4.98 g of tetramethylammonium hydroxide solution (25 wt. % in H$_2$O, 13.7 mmol) and 300.0 g of acetonitrile were charged into a 2 l three-necked round-bottomed flask equipped with magnetic stirrer, thermometer and condenser. The resulting non-homogeneous mixture was placed under dry nitrogen and heated at 70° C. under stirring. After 7 hours of reaction under stirring at an internal temperature of 70° C., the conversion was 28.7%, as confirmed by $^{19}$F-NMR spectroscopy. The reaction was stopped and the mixture was cooled down to room temperature. The mixture was washed first with distilled water (1200 g) and then three times with 1000 g distilled water and 20 g isobutanol. Every time the resulting two phases were vigorously stirred at room temperature for a few minutes and, after separation, the lower organic layer was collected. The solvents (isobutanol, acetonitrile and traces of water) were removed by distillation at 60° C. under reduced pressure (residual pressure=2 Pa) to afford 649 g crude product with a hydroxyl equivalent weight EW=769 g/eq and having formula:

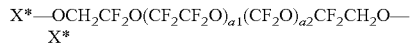

X*—OCH$_2$CF$_2$O(CF$_2$CF$_2$O)$_{a1}$(CF$_2$O)$_{a2}$CF$_2$CH$_2$O— X* where X*=H (71.3% on molar basis) or X*=(C$_6$H$_3$)(NO$_2$)$_2$ (28.7% on molar basis).

Step (b)—Preparation of a Mixture (M-2) from Mixture (M-1) and Hexachlorocyclophosphazene 647.7 g of mixture (M1) (EW=769 g/eq; 842 meq.) obtained from step (a) were charged into a 2 l three-necked round-bottomed flask equipped with magnetic stirrer, dropping funnel, thermometer and condenser, and then added with 29.4 g KOH (222.7 meq.; 42.5% solution in water). The mixture was heated to 80° C. and kept at this temperature under stirring, while vacuum was applied to the flask by means of a mechanical pump until complete elimination of water (about 40 minutes at P=2 Pa), to obtain a homogeneous solution. In a separated flask 5.9 g hexachlorocyclotriphosphazene (HCP, 102 meq.) was dissolved in 184 g 1,3-hexafluoroxylene (HFX). The resulting solution was transferred via a double-ended needle into the dropping funnel and slowly added to the solution of (M1) and KOH, under stirring at 77-78° C. during 4 hours. The reaction mixture was kept at this temperature under stirring, monitoring the conversion from time to time by $^{31}$P-NMR analysis. After 3 hours, the conversion was quantitative (singlet in the $^{31}$P-NMR spectrum at 17 ppm) and the reaction was stopped. After cooling at room temperature, the mixture was added with 143 g distilled water, 22 g HCl 37% w/w water solution and 21 g isobutyl alcohol. The two phases were vigorously stirred and, after separation, the lower organic layer was collected. A second washing was carried out with 500 g distilled water and 20 g isobutyl alcohol. After phase separation, the solvents (HFX and isobutyl alcohol) were removed by distillation at 80° C. under reduced pressure (P=2 Pa), to afford 636 g crude product which was submitted to thin-layer distillation. Through two passages at 160° C. (P=0.8 Pa) and 190° C. (P=0.8 Pa), two fractions of only unreacted mixture (M-1), as confirmed by the absence of signals in the $^{31}$P-NMR spectrum, were removed, leaving 161 g of a high boiling, low volatility residue, which was characterized by $^{19}$F-NMR, $^{1}$H-NMR and $^{31}$P-NMR. The residue was submitted to a further distillation step at 250° C. and P=0.8 Pa in order to quantitatively remove the unreacted mixture (M-1) as confirmed by GPC.

Step (c)—Fractionation of Mixture (M-2) with Supercritical Carbon Dioxide (scCO$_2$)

Mixture (M-2) obtained from step (b) was charged into a 300 ml SFT-150 Supercritical CO$_2$ Extraction System and heated at 100° C. Through a step-by-step pressure increase (from 18 to 40 MPa) and operating at a CO 2 flow rate of 4 Nl/min, 19 fractions were collected. Compound (L-2) and the corresponding spiro (L-2) and ansa (L-2) compounds were separated from the bridged by-products, which were selectively collected at high pressure. Each fraction was characterized by $^{31}$P-NMR, $^{19}$F-NMR, $^{1}$H-NMR, $^{13}$C-NMR and GPC. Fractions 10 to 12 (16.53 g) were pooled together and the ratio R between the P—OCH$_2$CF$_2$O— and the —OCF$_2$X end-groups (X=—CH$_2$OH, —CH$_2$O(C$_6$H$_3$)(NO$_2$)$_2$, —F or —H) measured by $^{19}$F-NMR and $^{1}$H-NMR. R was found to be 1.14, corresponding to a molar percent composition of 63% (L-2) and 37% spiro (L-2)+ansa (L-2). The molar ratio between —CH$_2$OH and —CH$_2$O(C$_6$H$_3$)(NO$_2$)$_2$ end-groups resulted to be 2.95.

The invention claimed is:

1. A compound (L) comprising a cyclophosphazene central core wherein each phosphorus atom of said core bears substituents independently selected from:
   a) a chain (A), said chain (A) comprising a (per)fluoropolyether chain [chain (R$_f$)], one or more aromatic or heteroaromatic moieties [moiety/ies (Ar$^m$)] and, optionally, one or more hydroxy groups and
   b) a chain (B), said chain (B) comprising a (per)fluoropolyether chain [chain (R$_f$)] and one or more hydroxy groups;
   with the proviso that at least one phosphorous atom of the central core is substituted with chain (A);
   wherein compound (L) is a compound of formula (L-1) below:

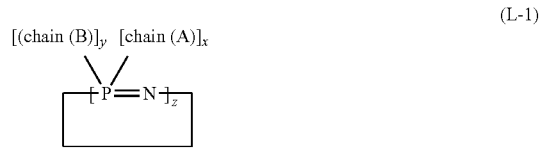

(L-1)

wherein:
x and y are 0, 1 or 2, with the proviso that x+y=2;
z is an integer of at least 3;
chain (A) complies with formula (A-1) below:

-G*-O—R$_f$-E*      (A-1)

wherein:
G* is is selected from formulae (i*) (vii*) below:

—(OCH$_2$CH$_2$)$_n$OCH$_2$XFC—;      (i*)

—[OCH(CH$_3$)CH$_2$)]$_n$OCH$_2$XFC—;      (ii*)

—(OCH$_2$CH$_2$)$_n$OCH$_2$CF$_2$CF$_2$—;      (iii*)

—[OCH$_2$CH(OH)CH$_2$]$_n$OCH$_2$XFC—;      (iv*)

—[OCH(CH$_2$OH)CH$_2$]$_n$OCH$_2$XFC—;      (v*)

—[OCH$_2$CH(OH)CH$_2$)$_n$OCH$_2$CF$_2$CF$_2$—; and      (vi*)

—[OCH(CH$_2$OH)CH$_2$]$_n$OCH$_2$CF$_2$CF$_2$—      (vii*)

wherein X is F or CF$_3$, n ranges from 0 to 5 and n' ranges from 1 to 3;

(E*) is selected from formulae (viii*)-(xii*) below:

—CFXCH$_2$O(CH$_2$CH$_2$O)$_n$(CH$_2$)$_p$Ar$^m$;      (viii*)

—CFXCH$_2$O[CH$_2$CH(CH$_3$)O]$_n$(CH$_2$)$_p$Ar$^m$;      (ix*)

—CF$_2$CF$_2$CH$_2$O(CH$_2$CH$_2$O)$_n$(CH$_2$)$_p$Ar$^m$;      (x*)

—CFXCH$_2$O[CH$_2$CH(OH)CH$_2$O]$_n$(CH$_2$)$_p$Ar$^m$ and      (xi*)

—CF$_2$CF$_2$CH$_2$O[CH$_2$CH(OH)CH$_2$O]$_n$(CH$_2$)$_p$Ar$^m$,      (xii*)

wherein X is F or CF$_3$, n and n' are as defined above, p is 0 or 1 and (Ar$^m$) is an aromatic or heteroaromatic moiety; and R$_f$ is a (per)fluoropolyether chain;
and wherein either (G*) or (E*) comprises the one or more aromatic or heteroaromatic moiety (Ar$^m$);
chain (B) complies with formula (B-1) below:

-G-O—R$_f$-E      (B-1)

wherein:
G** is selected from formulae (i*) (vii*) below:

—(OCH$_2$CH$_2$)$_n$OCH$_2$XFC—;      (i*)

—[OCH(CH$_3$)CH$_2$)]$_n$OCH$_2$XFC—;      (ii*)

—(OCH$_2$CH$_2$)$_n$OCH$_2$CF$_2$CF$_2$—;      (iii*)

—[OCH$_2$CH(OH)CH$_2$]$_n$OCH$_2$XFC—;      (iv*)

—[OCH(CH$_2$OH)CH$_2$]$_n$OCH$_2$XFC—;      (v*)

—[OCH$_2$CH(OH)CH$_2$)$_n$OCH$_2$CF$_2$CF$_2$—; and      (vi*)

—[OCH(CH$_2$OH)CH$_2$]$_n$OCH$_2$CF$_2$CF$_2$—      (vii*)

wherein X is F or CF$_3$, n ranges from 0 to 5 and n' ranges from 1 to 3;

(E) is selected from formulae (viii)-(xii**) below:

—CFXCH$_2$O(CH$_2$CH$_2$O)$_n$H;      (viii**)

—CFXCH$_2$O[CH$_2$CH(CH$_3$)O]$_n$H;      (ix**)

—CF$_2$CF$_2$CH$_2$O(CH$_2$CH$_2$O)$_n$H;      (x**)

—CFXCH$_2$O[CH$_2$CH(OH)CH$_2$O]$_n$H and      (xi**)

—CF$_2$CF$_2$CH$_2$O[CH$_2$CH(OH)CH$_2$O]$_n$H,      (xii**)

wherein X is F or CF$_3$ and n and n' are as defined above; and

R$_f$ is a (per)fluoropolyether chain.

2. The compound according to claim 1 wherein chain (R$_f$) in chains (A) and (B) is a fully or partially fluorinated polyoxyalkylene chain that comprises repeating units R°, said repeating units being independently selected from the group consisting of:

(i) —CFXO—, wherein X is F or CF$_3$,
(ii) —CFXCFXO—, wherein X, equal or different at each occurrence, is F or CF$_3$, with the proviso that at least one of X is —F,
(iii) —CF$_2$CF$_2$CW$_2$O—, wherein each of W, equal or different from each other, are F, Cl, H,
(iv) —CF$_2$CF$_2$CF$_2$CF$_2$O—, and
(v) —(CF$_2$)$_j$—CFZ—O— wherein j is an integer from 0 to 3 and Z is a group of general formula —OR$_f'$T, wherein R$_f'$ is a fluoropolyoxyalkene chain comprising a number of repeating units from 0 to 10, said recurring units being selected from: —CFXO—, —CF$_2$CFXO—, —CF$_2$CF$_2$O—, —CF$_2$CF$_2$CF$_2$O—, with each of each of X being independently F or CF$_3$ and T being a C$_1$-C$_3$ perfluoroalkyl group.

3. The compound according to claim 2 wherein chain (R$_f$) complies with formula (R$_f$-III) here below:

—(CF$_2$CF$_2$O)$_{a1}$(CF$_2$O)$_{a2}$—      (R$_f$-III)

wherein:
a1, and a2 are integers >0 such that the number average molecular weight is between 400 and 10,000, with the ratio a2/a1 being comprised between 0.1 and 10.

4. The compound according to claim 1 wherein z is 3 or 4.

5. The compound according to claim 1 wherein (Ar$^m$) is phenyl or pyridyl bearing one or more substituents independently selected from fluorine, trifluoromethyl and nitro.

6. The compound according to claim 1 wherein:
(G*) and (G**) are selected from:
formula (i*) —(OCH$_2$CH$_2$)$_n$OCH$_2$XFC—, wherein X is F and n is selected from 0, 1 and 2; and
formula (iv*) —[OCH$_2$CH(OH)CH$_2$]$_n$OCH$_2$XFC—, wherein X is F and n' is (E*) is selected from:
formula (viii*) —CFXCH$_2$O(CH$_2$CH$_2$O)$_n$(CH$_2$)$_p$Ar$^m$, wherein X is F, n is selected from 0, 1 and 2, p is 0 and (Ar$^m$) is phenyl or pyridyl bearing one or more substituents independently selected from fluorine, trifluoromethyl and nitro; and
formula (xi*) —CFXCH$_2$O[CH$_2$CH(OH)CH$_2$O]$_n$(CH$_2$)$_p$Ar$^m$, wherein X is F, n' is 1, p is 0 and (Ar$^m$) is phenyl or pyridyl bearing one or more substituents independently selected from fluorine, trifluoromethyl and nitro;
and (E**) is selected from
formula (viii**) —CFXCH$_2$O(CH$_2$CH$_2$O)$_n$H, wherein X is F and n is selected from 0, 1 and 2; and
formula (xi**) —CFXCH$_2$O[CH$_2$CH(OH)CH$_2$O]$_n$H, wherein X is F and n' is 1.

7. A mixture comprising a compound of claim 1 and one or more compounds comprising a cyclophosphazene central core wherein each phosphorus atom of said core bears substituents independently selected from:
a) a chain (A), said chain (A) comprising a (per)fluoropolyether chain [chain (R$_f$)], one or more aromatic or heteroaromatic moieties (Ar$^m$) and, optionally, one or more hydroxy groups and b) a chain (B), said chain (B) comprising a (per)fluoropolyether chain [chain ($R_f$)] and one or more hydroxy groups and c) at least one chain (B'), said chain (B') comprising a (per)fluoropolyether chain ($R_f$), wherein both ends of chain ($R_f$) are bound either to a same phosphorus atom of the cyclophosphazene ring or to two different phosphorus atoms of the cyclophosphazene ring via a bridging group (G), said group (G) comprising one or more aromatic or heteroatomatic moieties and/or one or more hydroxy groups, with the proviso that at least one chain (A), or at least one chain (B') wherein bridging group (G) comprises one or more aromatic or heteroaromatic moieties, (Ar''') is present.

8. A lubricant composition comprising one or more compounds of claim 1.

9. A method for lubricating sliding or moving parts of a magnetic recording medium comprising applying to said parts the composition of claim 8.

10. A magnetic recording medium comprising a sliding or moving part having applied thereto the composition of claim 8.

\* \* \* \* \*